(12) United States Patent
Soh

(10) Patent No.: US 11,804,293 B2
(45) Date of Patent: Oct. 31, 2023

(54) RAPID WEARABLE DATA-DRIVEN BIOELECTRONICS DEVICE AND PLATFORM FOR FOOD FRESHNESS MONITORING

(71) Applicant: Annie Mafotsing Soh, Breinigsville, PA (US)

(72) Inventor: Annie Mafotsing Soh, Breinigsville, PA (US)

( * ) Notice: Subject to any disclaimer, the term of this patent is extended or adjusted under 35 U.S.C. 154(b) by 95 days.

(21) Appl. No.: 17/074,335

(22) Filed: Oct. 19, 2020

(65) Prior Publication Data

US 2021/0366590 A1    Nov. 25, 2021

Related U.S. Application Data

(60) Provisional application No. 63/078,351, filed on Sep. 15, 2020, provisional application No. 63/062,516, filed on Aug. 7, 2020, provisional application No. 63/028,220, filed on May 21, 2020.

(51) Int. Cl.

| | |
|---|---|
| *G09B 19/00* | (2006.01) |
| *G16H 20/60* | (2018.01) |
| *G06F 1/16* | (2006.01) |
| *G06N 20/00* | (2019.01) |
| *G06F 18/24* | (2023.01) |
| *G06F 18/214* | (2023.01) |

(Continued)

(52) U.S. Cl.
CPC ............ *G16H 20/60* (2018.01); *G06F 1/163* (2013.01); *G06F 18/2155* (2023.01); *G06F 18/24* (2023.01); *G06N 20/00* (2019.01); *G06V 10/764* (2022.01); *G06V 10/774* (2022.01)

(58) Field of Classification Search
None
See application file for complete search history.

(56) References Cited

U.S. PATENT DOCUMENTS

| 9,349,297 | B1 * | 5/2016 | Ortiz ................. G06K 9/6215 |
| 10,971,031 | B2 * | 4/2021 | Ortiz ................... G09B 19/00 |
| 2003/0076983 | A1 * | 4/2003 | Cox .................... G16H 20/60 |
| | | | 382/110 |

(Continued)

OTHER PUBLICATIONS

Machine Learning Driven Approach Towards the Quality Assessments of Fresh Fruits using Non-invasive Sensing, IEEE Journal, Feb. 15, 2020, Aifen Ten; Adnan Zahid.

(Continued)

*Primary Examiner* — Sunit Pandya
(74) *Attorney, Agent, or Firm* — Keri Sicard; David Krivoshik

(57) ABSTRACT

The present application relates to the use of soft nano material integrated to micro-electronics circuit to detect signals from nutritional substances and the subsequent conversion of these signals into format suitable for a trained machine learning model through pre-processing steps prior to sending to the machine learning model as well as the output format of the machine learning model and post processing in order to obtain a final determination of the quality and predicted expiration date of a nutritional substance within a probabilistic confidence level. The application encompasses a soft nano-material integrated with micro-electronics for signal capture and an analytics platform for machine learning model training, classification and prediction with a probabilistic confidence level result.

24 Claims, 10 Drawing Sheets

(51) Int. Cl.
*G06V 10/764* (2022.01)
*G06V 10/774* (2022.01)

(56) References Cited

U.S. PATENT DOCUMENTS

| | | | |
|---|---|---|---|
| 2012/0208151 A1* | 8/2012 | Culver | G06Q 10/087 |
| | | | 434/127 |
| 2016/0350704 A1* | 12/2016 | Minvielle | G06Q 10/087 |
| 2020/0008299 A1 | 1/2020 | Tran | |
| 2020/0152312 A1* | 5/2020 | Connor | A61B 5/11 |

OTHER PUBLICATIONS

Freshness of Food Detection using IoT and Machine Learning, IEEE Journal, Apr. 27, 2020, Nachiketa Hebbar, ARN #:9077712.
A CMOS Fish Freshness to Continuous-Time Incremental Sigma-Delta Modulator for Monitoring Fish Freshness in Fish Markets, IEEE Journal, 2019, Cheng-Ta Chiang, Loan-Teng.
Monitoring the Freshness Level of Beef Using Nanocomposite Gas sensors in Electronic Nose, IEEE Journal, 2019, Mon Myat Swe; Tanthip Eamsa-Ard;Toemsak Srikhirin;.
DoFP-ML: A Machine Learning Approach to Food Quality Monitoring Using a DoFP-Polarization Image Sensor, IEEE Journal, 2020, Maen Takruri; Abubakar Abubakar; Noora Alnaqbi;.
Mobile cloud based system recognizing nutrition and freshness of food image, IEEE Journal, 2017, Diptee Kumbhar; Sarita Patil.
Monitoring and Detection of Fruits and vegetables Spoilage in the Refrigerator Using Electronic Nose Based on Principal Component Analysis, IEEE, 2019, Yeo Vincent C. Caya.
Intelligent Processing of E-nose Information for Fish Freshness Assessment, IEEE Journal, 2007, H. Gholamhosseini; Dehan Luo; Hongxiu Liu.
Flexible, Wearable, and Stretchable Electronics, Book, Date: 2020, CRC Press Young-Tae Kwon et Woon-Hong Yeo.
Advanced Nanomaterials, Printing Processes, and Applications for Flexible Hybrid Electronics, MDPI Materials Journal, 2020, S. Park, H. Kim, W.H. Yeo.

\* cited by examiner

RAPID WEARABLE DATA-DRIVEN BIOELECTRONICS DEVICE AND PLATFORM FOR FOOD FRESHNESS MONITORING

TECHNICAL FIELD

The present application relates generally to a method of monitoring food freshness and more specifically to the use of soft nano material integrated to a micro-electronics circuit to detect signals from nutritional substances and the subsequent conversion of these signals into format suitable for a trained machine learning model to obtain a determination of the quality and predicted expiration date of a nutritional substance within a probabilistic confidence level.

BACKGROUND

Millions of customers around the world buy nutritional substances such as meat, aquatic products, fruits, vegetables every day from food retail surfaces for consumption. However, these nutritional substances are often thrown out or discarded prior to the spoilage date. The early discharge is often due to the confusion of several dates such as 'best by', 'sell by' or 'expiration date' stamped and labeled on the product's packaging. Moreover, situations such as the COVID-19 pandemic have led to the destruction of thousands of egg-laying hens and other essential nutritional substances because of lack of demand from closed restaurants. This situation has created a need for improving access to fresh, healthy food through food retail surfaces across urban, rural and underserved communities.

Discarded, edible nutritional substances can be re-routed to food retailers, food distributors or direct to consumer markets to avoid landfilling and over time releasing toxic methane that fosters global warming.

From the traveling industry arena, international travelers with nutritional substances in their luggages are often subject to substance inspection through customs with various nutritional substances being discarded while still fresh and consumable.

SUMMARY

With food insecurity being a major problem in light of the COVID-19 pandemic stemming from the high demand for essential nutritional substances, less arable land for agriculture given global climate change impact on lands, a cost-effective soft nano material integrated with micro-electronics component to detect and capture signals from nutritional substances for subsequent conversion of these signals into format suitable for a trained machine learning model through particular pre-processing steps as well as the post-processing of the outputs in order to monitor and evaluate food quality, could help alleviate the problem.

The benefits of the proposed soft nano-material enabled bio-electronics coupled to a bio-analytics platform include monitoring and evaluating customers' nutritional substances with the objectives of reducing food waste and loss, avoiding food poisoning at the households, businesses and communities levels while contributing to the United Nations and United States EPA/USDA 2030 food sustainability goals. Such soft nano-material enabled bio-electronics and bio-analytics platform may contribute to global Food and Loss reduction credits initiatives to raise each customer awareness to his/her own food waste footprint and to implement incentives through Food Loss and Waste credits to reduce that footprint.

In an aspect of the present invention, a computer-implemented method for determining nutritional value is disclosed. The method comprises: receiving, by one or more computing devices, signals that represent properties of the nutritional substance; the signals being obtained from one or more nano membrane electrodes of a soft nano-material enabled bio-electronics adhesive on or in a nutritional substance; pre-processing the signals into digital signals by time-frequency signal processing; extracting temporal and impulse response features from the digital signals; using one or more machine learning algorithms to convert the extracted features into output values by a trained temporal learning model; post-processing the output values by threshold value decision making in order to determine the nutritional value; and displaying the nutritional value properties to a user interface.

In another aspect of the present invention, one of more of the following steps may be disclosed: (i) wherein properties of said signals of the nutritional substance are electrical, visual and volatile organic compound properties, (ii) wherein the electrical, visual and volatile organic compound properties include temperature, humidity, weight, position, image, capacitive fluid level, gas concentration, gas sample rate constant, clock time, resonant frequency, impedance frequency, impedance phase angle, voltage range, (iii) wherein the signals obtained from one or more nano membrane electrodes of a soft nano-material enabled bio-electronics adhesive on or in a nutritional substance are forwarded to the soft nano material sensors for pre-processing, (iv) wherein pre-processing the signals comprises: sampling the signals; amplifying the signals; applying fractional conductance to reduce an effect of the sensor drift; applying a model to smooth a digital signal output response curve; determining an identity of the nutritional substance from the received signals; determining a position of the nutritional substance from the received signals; determining the molar concentration and sample rate constant of the volatile organic compound from the received signals, (v) wherein converting the extracted features into the output values by a trained temporal learning model comprises using fresh nutritional substance input data to train a machine learning model to obtain a monitoring model; delivering freshness level grading models by using a nutritional substance input data over continuous sampled period of time and different storage temperature conditions to obtain freshness level grading models; determining an evaluation model based on the monitoring model and the freshness level grading models, (vi) wherein the temporal learning model is trained by the steps comprising randomly initializing a model into an initial model, separating incoming fresh nutritional samples data into several segments, estimating a Gaussian mixture parameters within each segment, re-estimating the initial model to an estimated model, determining the trained temporal learning model based on convergence, wherein convergence is determined when a distance between the initial model and the estimated model reaches a threshold, (vii) wherein the temporal learning model comprises fresh nutritional samples data measured at a time of purchase of the samples, (viii) wherein the freshness level grading models comprise nutritional samples separated into three groups comprising fresh nutritional samples stored under refrigerator temperature; fresh nutritional samples measured every 8 hour under refrigerator storage temperature; and fresh nutritional samples measured every 8 hour under normal room storage temperature, (ix) wherein post-processing the output values comprises determining the nutritional value based on the monitoring model and the freshness level grading models for each freshness level, wherein the number of freshness level represents a highest value of all the freshness level grading models, (x) wherein the threshold value decision making is obtained by labeling the nutritional value, (xi) wherein labeling the nutritional value comprises deriving a nutritional label, a predicted expiration date value and a probabilistic confidence level value computed based on the monitoring model, and the freshness level grading models, (xii) wherein displaying the nutritional value properties comprises of displaying at least one of the nutritional substance name, the nutritional substance label value, the nutritional substance predicted expiration date, the nutritional substance location data points based on the signals received from the nutritional substance.

In a further aspect, a non-transitory computer-readable storage medium may be disclosed. The non-transitory computer readable storage medium may store a program which, when executed by a computer system, causes the computer system to perform a procedure comprising: receiving, by one or more computing devices, signals that represent properties of the nutritional substance; the signals being obtained from one or more nano membrane electrodes of a soft nano-material enabled bio-electronics adhesive on or in a nutritional substance; pre-processing the signals into digital signals by time-frequency signal processing; extracting temporal and impulse response features from the digital signals; using one or more machine learning algorithms to convert the extracted features into output values by a trained temporal learning model; post-processing the output values by threshold value decision making in order to determine the nutritional value; and displaying the nutritional value properties to a user interface.

In an even further aspect, a system for determining nutritional value may be disclosed, the system comprising at least one processor configured to perform the method comprising: receiving, by one or more computing devices, signals that represent properties of the nutritional substance; the signals being obtained from one or more nano membrane electrodes of a soft nano-material enabled bio-electronics adhesive on or in a nutritional substance; pre-processing the signals into digital signals by time-frequency signal processing; extracting temporal and impulse response features from the digital signals; using one or more machine learning algorithms to convert the extracted features into output values by a trained temporal learning model; post-processing the output values by threshold value decision making in order to determine the nutritional value; and displaying the nutritional value properties to a user interface.

In yet another aspect, one or more of the following configurations may be disclosed: a configuration (i) wherein the signals obtained from one or more nano membrane electrodes of a soft nano-material enabled bio-electronics adhesive on or in a nutritional substance are forwarded to the soft nano material sensors for pre-processing, (ii) wherein pre-processing the signals further comprises: sampling the signals; amplifying the signals; applying fractional conductance to reduce an effect of the sensor drift; applying a model to smooth a digital signal output response curve; determining an identity of the nutritional substance from the received signals; determining a position of the nutritional substance from the received signals; determining the molar concentration and sample rate constant of the volatile organic compound from the received signals, (iii) wherein the extracted features are converted into the output values by using fresh nutritional substance input data to train a machine learning model to obtain a monitoring model; delivering freshness level grading models by using a nutritional substance input data over continuous sampled period of time and different storage temperature conditions to obtain freshness level grading models; determining an evaluation model based on the monitoring model and the freshness level grading models, (iv) wherein the temporal learning model is trained by the steps comprising randomly initializing a model into an initial model, separating incoming fresh nutritional samples data into several segments, estimating the Gaussian mixture parameters within each segment, re-estimating the initial model to an estimated model, determining the trained temporal learning model based on convergence, wherein convergence is determined when the distance between the initial model and the estimated model reaches a threshold.

BRIEF DESCRIPTION OF THE DRAWINGS

The accompanying drawings illustrate embodiments and/or aspects of the disclosure and, together with the written description, serve to explain the principles of the disclosure. Wherever possible, the same reference numbers are used throughout the drawings to refer to the same of like elements of an embodiment, and wherein.

DETAILED DESCRIPTION

The terms "soft nano-enabled bio-electronics", "soft nano-material enabled bio-electronics", "soft-electronics", "bio-electronics", "soft nano-enabled bio-electronics", "soft nano-material enabled bioelectronics" refer to the same term or object and are used interchangeably. These terms refer to network-enabled devices comprising a thick, lightweight, stretchable, non-obtrusive, waterproof polymeric substrate material that is adhesive on or in the nutritional substance and integrated with thin film structures and/or nano-membranes electrodes to capture nutritional substances signals and integrated to micro-electronics circuit component. There is no restriction on the location where such device is positioned or materials and configurations that have to be used. The term 'soft' used herein refers to comfortable for adhesion on or in the nutritional substance. The substrate materials of the soft nano-enabled bio-electronics can be made of bioresorbable and biodegradable materials. The term 'bioresorbable' refers to eliminating environmental, chemical and physical damages in a way that the constituent materials dissolve, disintegrate or decompose without environmental and toxic residue after using the micro-electronics. The term 'biodegradable' refers to the constituent materials dissolving, disintegrating or decomposing over a short period of time. The term 'semiconductors, dielectric, conductors and multiple hybrid sensors' used herein generally refers to the electronics circuit component or chips layer including one of the miniaturized sensors, signal acquisition and processing module, communication-based micro-controller module, resonators, among other electronics components. The term 'nutritional substance' used herein generally refers to any solid, liquid or semi-liquid food product, plant, nuts, seeds, flour, beverage or the like. The term 'signals' used herein refer to the electrical, visual and volatile organic compound properties of the nutritional substance including temperature, humidity, weight, position, image, capacitive fluid level, gas concentration, gas sample rate constant, clock time, resonant frequency, impedance frequency, impedance phase angle, voltage range. The term 'nutritional substance location data points' used herein refers to the longitude and latitude position of the nutritional substance. The term 'nutritional value properties' used herein refers to at least one of the nutritional substance name, the nutritional substance label value, for example 'spoiled', or 'nutritious', the nutritional substance predicted expiration date and the nutritional substance location data points.

Figure 1:
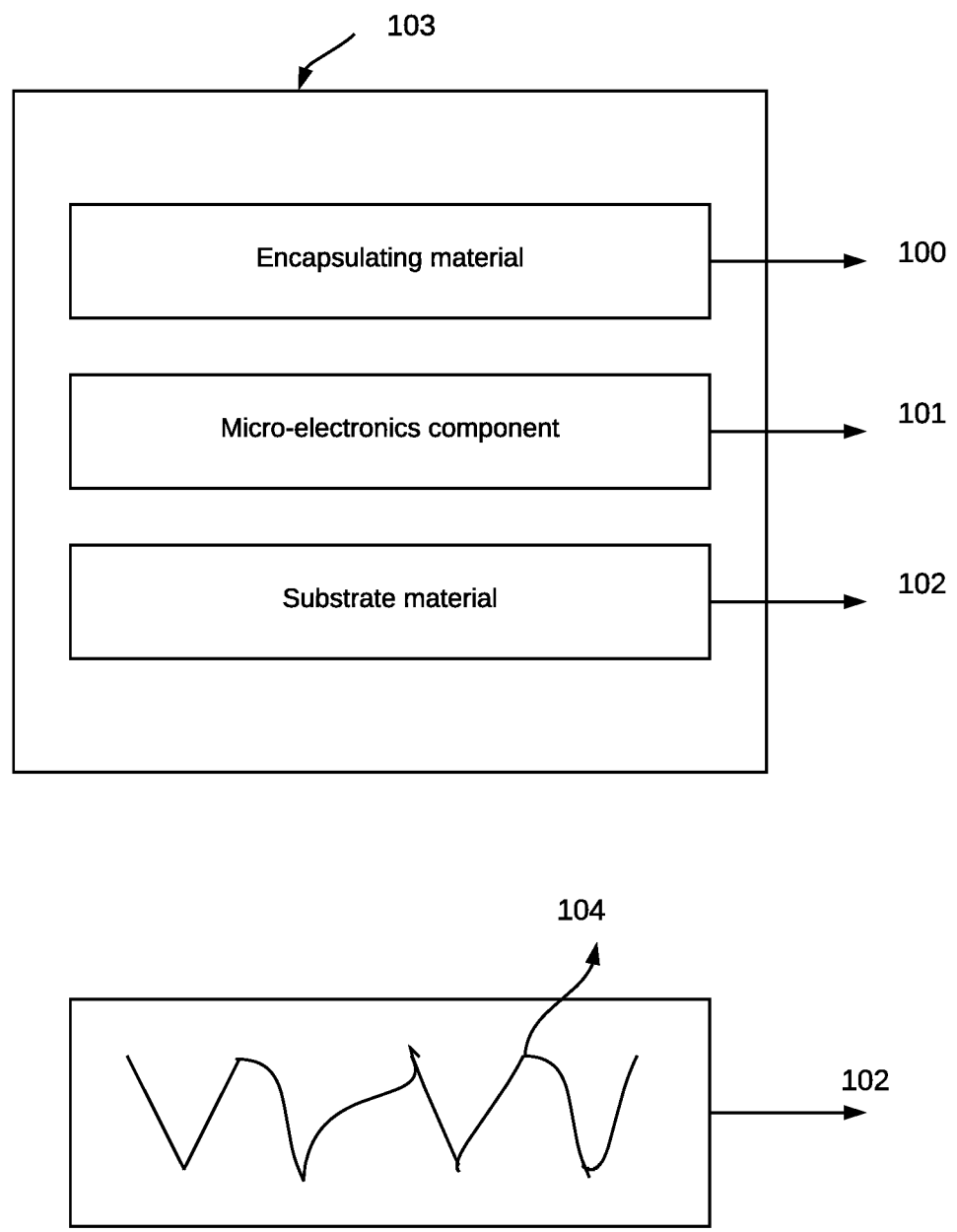
FIG. 1 is a schematic diagram illustrating the various components of the soft nano-material enabled bioelectronics.

FIG. 1 is a schematic diagram illustrating the various components of the soft nano-material enabled bioelectronics for the nutritional substance quality monitoring, evaluation and expiration date value prediction. The soft nano-material enabled bioelectronics 103 encompasses three layers: the encapsulating material, 100, the micro-electronics component, 101 and the substrate material 102.

The encapsulating material, 100, is the layer that affords waterproof resistance to the bio-electronics. It can be made of polymeric materials that extend the operational timeframe or lifetime of the bio-electronics. The micro-electronics component, 101, is the layer integrated with semiconductors, dielectric, conductors and multiple hybrid sensors to receive signals from the sample nutritional substance adhesive to the substrate material 102. The substrate material, 102, is a polymeric material at the micrometer or nanometer scale affixed to or in the nutritional substance. The said substrate material can be made of natural materials or the like.

The substrate material 102 of the soft nano-material enabled bioelectronics 103 is affixed to or in the nutritional substance. The nano membrane electrodes 104, with high electrical conductivity, detect and capture signals from the nutritional substance. These signals are communicated first to the sensors' array of the micro-electronics component 101, and then communicated to the communication module of the micro-electronics component 101. The communication module communicates the received signals to the bio-analytics platform over a network (not illustrated).

Figure 9:
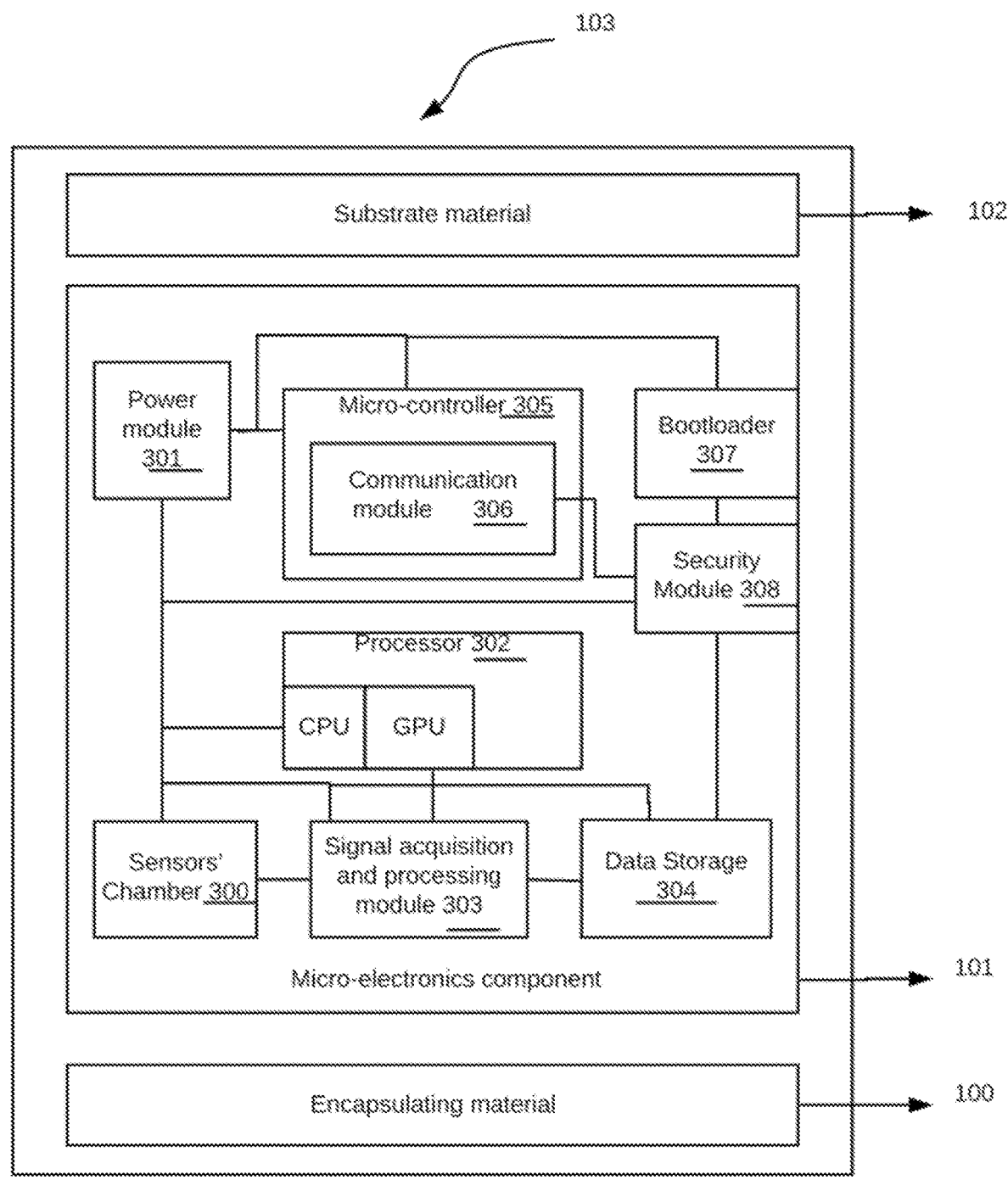
FIG. 9 is a schematic diagram illustrating the elements of the micro-electronics component of the soft nano-material enabled bio-electronics.

FIG. 9 is a schematic diagram illustrating the elements of the micro-electronics component of the soft nano-material enabled bio-electronics. This component comprises the micro-electronics necessary for capturing, amplifying, processing and communicating the signals received from the nutritional substance.

The soft nano-material enabled bioelectronics, 103, comprises three layers: the encapsulation material layer, 100, the micro-electronics component, 101, and the substrate material 102. The micro-electronics component 101 further comprises sensors' chamber 300 encompassing an array of sensors ranging from CMOS image sensor, weight sensor, position sensor, capacitive fluid level sensor, Volatile Organic Compound (VOC) gas sensors, temperature sensor, humidity sensor to Inductance-Capacitance resonators, Surface Plasmon resonators, clock time sensor and Quartz Tuning Forks (QTF) sensors. These sensors are used to receive the nutritional substance signals detected and captured from the nano-membrane electrodes 104 on the substrate material 102.

In one example, the nutritional substance, 400, is a food product such as an apple. The food product can be located on a plate in a home kitchen table; at a food service business establishment; at a food supply chain inspection conveyor at a cross-border port of entry; at a food production establishment or at a food manufacturing establishment. The nutritional substance can be a food product or agricultural product such as one of the poultry, beef, pork, turkey, lamb, fish, shrimp, an egg, cheese, milk, a banana, a tomato, flour, among other food or beverage products. The soft nano-material enabled bio-electronics 103 is applied to the skin of the food product manually or using a machine automation process. The substrate material 102 of the soft nano-material enabled bio-electronics 103 is adhesive to the skin of the food product as a patch. Nano-membrane electrodes 104 with high electrical conductivity located on the substrate material 102 enable the transmission of electrical properties in one of the (KHz, GHz, MHz, THz) electromagnetic wave spectrum frequencies, among other frequencies, and peak voltage range from the food product to the sensors located on the micro-electronics component 101 of the bio-electronics device.

In addition, target VOC molecules on the food product are adsorbed onto the substrate material polymer 102, a film of Molecularly Imprinted Polymer (MW) selective and sensitive to one of the target gas including Hydrogen, Ethanol, Hydrocarbons, Hydrogen Sulfide, Ammonia, Trimethyl Amine, Methyl Mercaptan, Methane, Iso-butane, Propane, Carbon Monoxide (CO), among other VOC gases. A change in resonant frequency induced from loaded mass change onto the QTF sensor detects and measures the concentrations of VOCs present on or in the food product. The signals captured from the substrate material 102 adhesive to or in the food product and communicated to the sensors using the nano-membrane electrodes 104 are amplified and communicated to a signal acquisition and processing module responsible for pre-processing the signals into digital signals by time-frequency signal processing. Moreover, CMOS image sensor captures the light from the food product and converts it into electrical signals. The position sensor captures and forwards the indoor or outdoor longitude and latitude location data points of the nutritional substance. The soft nano-material enabled bio-electronics, 103, may be immersed in a semi-liquid or liquid food object or beverage to detect and capture the properties of the food or beverage product. The encapsulating material, 100, serves as a barrier to protect the micro-electronics component and power supply from fluid penetration.

The micro-electronics component 101 further comprises an array of sensors in a chamber 300; a signal acquisition and processing module 303 for time-frequency signal processing, a data storage 304 that stores the digital signals to be processed by machine learning models deployed on the micro-controller 305; the power module 301 providing power supply to all elements of the micro-electronics component, the processor 302 encompassing a Central Processing Unit (CPU) and a Graphical Processing Unit (GPU) for processing the digital signals at the edge (locally), a communication module 306 to communicate the digital signals over the network (not illustrated), a bootloader 307 flashed on the micro-controller 305 for receiving Over The Air (OTA) updates including one of the security patches and machine learning pre-trained models, among other OTA updates and pre-trained machine learning models; the security module 308 used to encrypt the digital signals both at the edge and while leaving the micro-electronics component 101 to the network (not illustrated).

Figure 4:
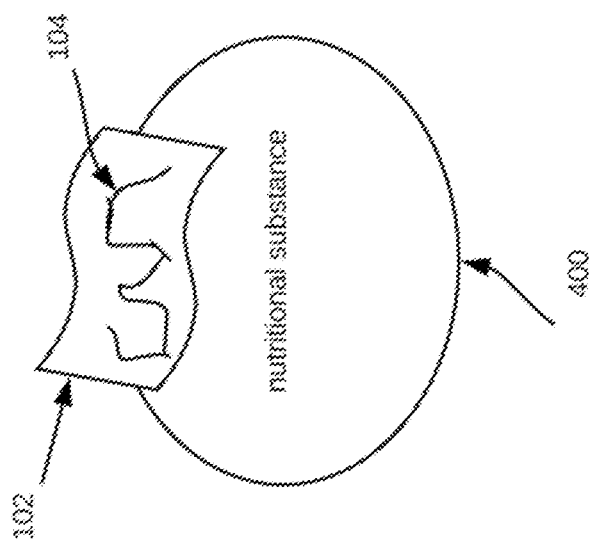
FIG. 4 is a schematic diagram describing a sample soft nano-material enabled bioelectronics adhering to a sample nutritional substance.

FIG. 4 is a schematic diagram describing the substrate material 102 of a soft nano-material enabled bioelectronics adhering to a sample nutritional substance 400. The substrate material 102 is a film of MIP selective and sensitive to target VOCs and encompasses nano-membrane electrodes 104 enabling the transfer of signals from a sample nutritional substance 400 to the micro-electronics component 101 of the soft nano-material enabled bio-electronics 103 (not illustrated).

Figure 10:
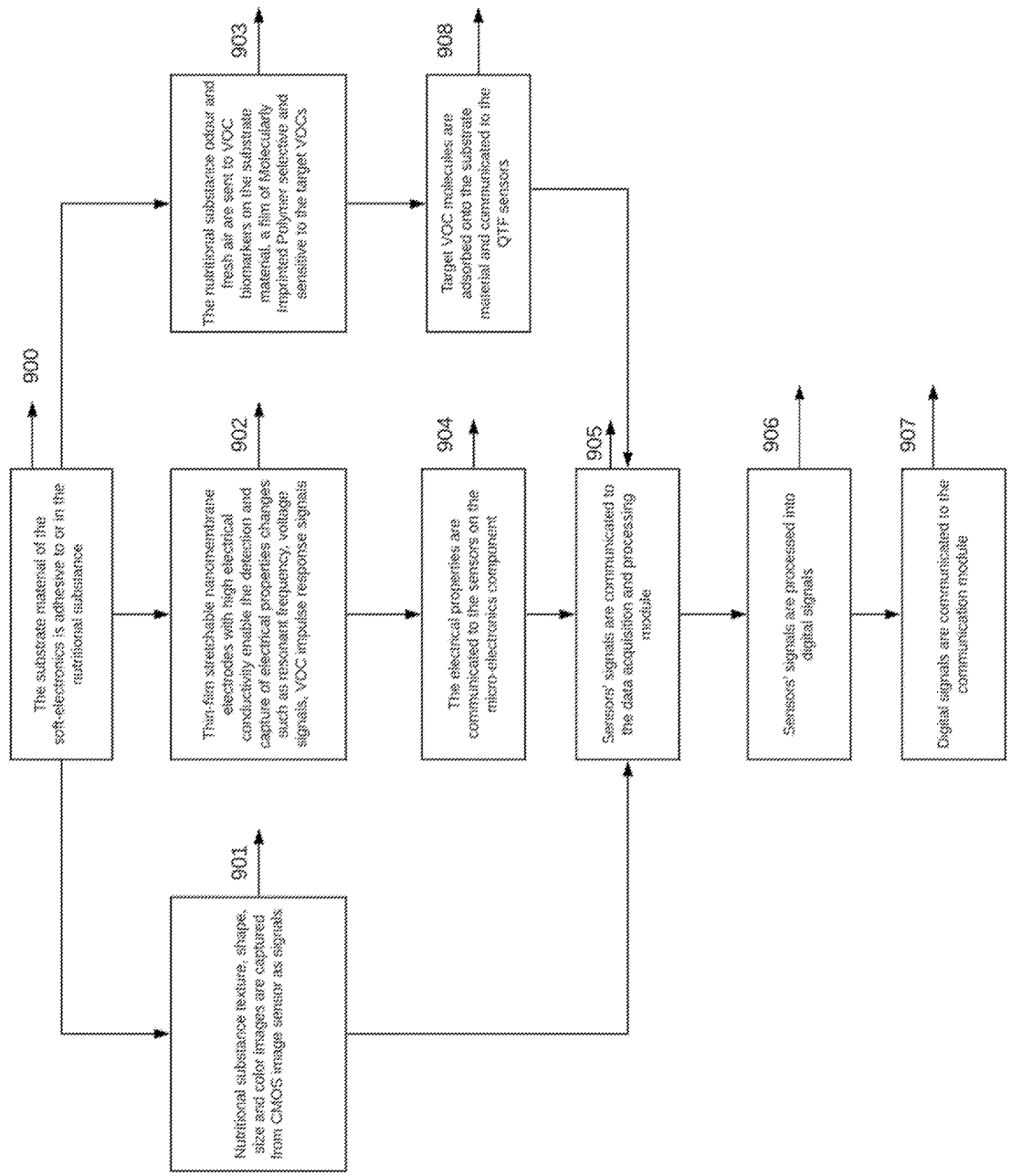
FIG. 10 is a flowchart diagram describing the flow process of signals captured from the nutritional substance to the soft nano-material layer of the bio-electronics.

FIG. 10 is a flowchart diagram describing the flow process of signals captured from the nutritional substance to the soft nano-material layer of the bio-electronics. In order to monitor, evaluate the nutritional substance quality and predict the nutritional substance expiration date, signals from the nutritional substance are detected and captured from the substrate material of the soft-electronics. The said substrate material is first affixed to the skin of the nutritional substance or in the substance 900. Then, three signal types including one of the electrical signals, visual signals and volatile organic compound signals are collected from the nutritional substance. The electrical, visual and volatile organic compound signals represent the electrical, visual and volatile organic compound properties of the nutritional substance. The nano-membrane electrodes on the substrate material enable the detection and capture of the change of electrical properties 902 for signal processing. The captured electrical properties are communicated to the sensors located on the micro-electronics component 904. The nutritional substance visual properties such as texture, shape, size and color are captured in 2-dimensional feature vectors from the CMOS imaging sensor 901 located in the micro-electronics component of the soft electronics. Volatile Organic Compounds properties are captured in parallel with the visual and electrical properties described above. The nutritional substance odour and fresh air are collected and communicated to the VOC biomarkers on the substrate material 903, a film of Molecularly Imprinted Polymer selective and sensitive to the target VOCs. These target VOC molecules are adsorbed onto the substrate material and communicated to the QTF sensors 908. Finally, the collected target VOC molecules 908 along with the VOC electrical impulse response signals, the visual signals 901 and electrical signals 904 are communicated first to the signal acquisition and processing module 905. The communicated signals are processed into digital signals 906 by time-frequency signal processing and subsequently communicated to the communication module 907 of the soft nano-material layer of the bio-electronics.

Figure 2:
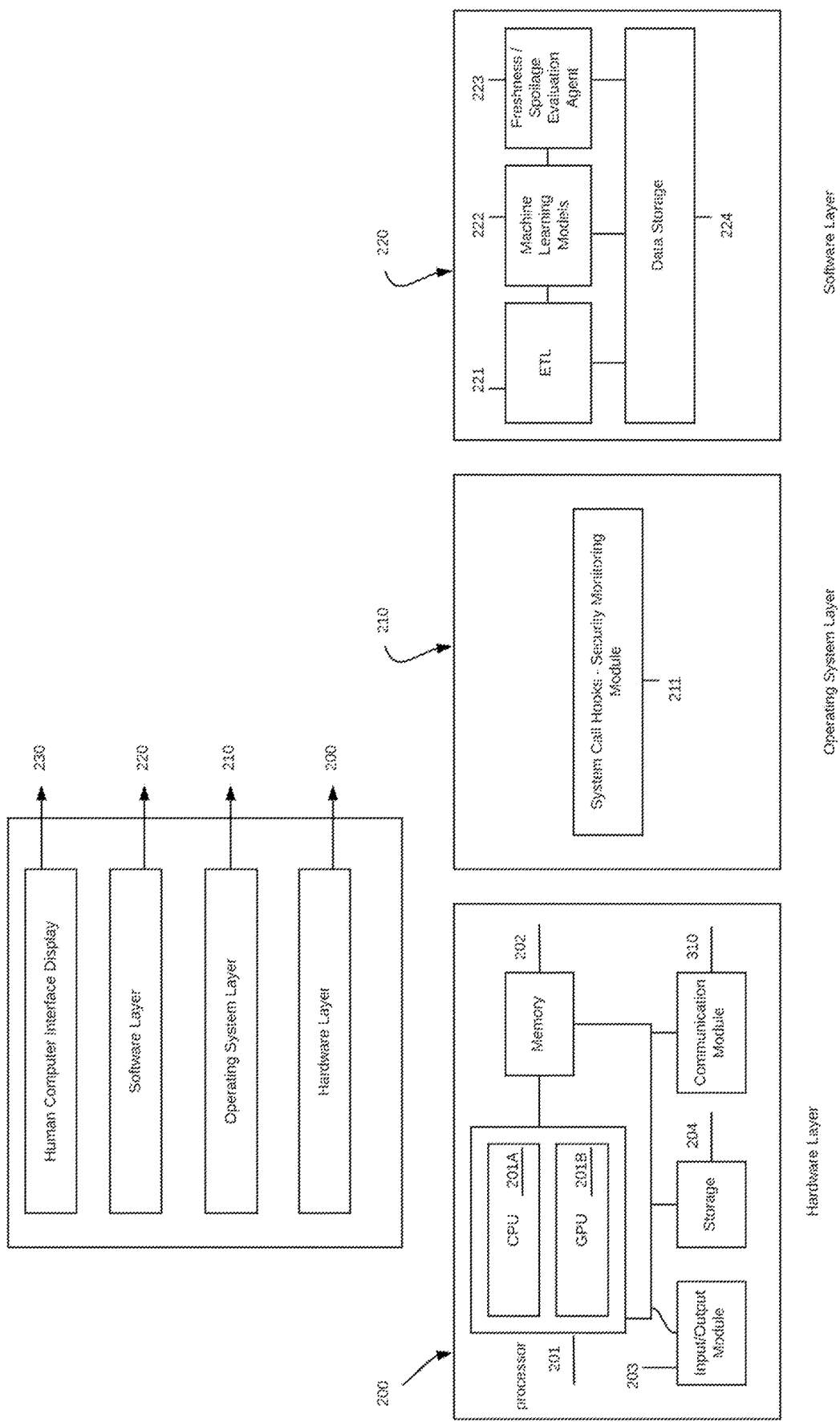
FIG. 2 is a schematic diagram illustrating the various components of the bio-analytics platform.

FIG. 2 is a schematic diagram illustrating the various components of the bio-analytics platform used for storing, processing and displaying the signals from the nutritional substance to a Human Computer User Interface.

The schematic diagram comprises the hardware layer, 200, that encompasses the processing and memory low-level resources needed to process the digital signals received over the network from the soft nano-material enabled bioelectronics; the operating system layer, 210, that mediates the synchronization and communication of nutritional substance digital signals between the hardware layer 200 and the software layer, 220. The operating system layer, 210, also comprises system call hooks 211 responsible for monitoring the platform program execution in order to detect anomalous behaviors; the software layer, 220, comprises a data storage with digital signals received from the operating system layer 210, the machine learning algorithms and artificial intelligent agent responsible for determining a nutritional substance label, for example, 'fresh', 'frozen', 'organic', 'nutritious' or 'spoiled', predicting an expiration date, for example, '3 days and 4 hours' and providing a probabilistic confidence level value, for example, '90%' based on the digital signals received from the operating system layer 210 and one or more threshold values delineating nutritional substance freshness and spoilage characteristics.

The Human Computer Interface (HCI) Display, 230, displays at least one of the digital signals from the nutritional substance, the configuration settings of the micro-electronics component of the soft nano-material enabled bioelectronics. The said HCI Display and configuration settings enable user input interaction between the soft nano-material enabled bioelectronics circuit component and the bio-analytics platform. The nutritional substance's digital signals are pre-processed and features extracted using Extract-Transform-Load (ETL) framework 221, processed using the machine learning models 222 and evaluated for freshness and/or spoilage (expiration) levels by an Evaluation Agent 223 on the platform in order to determine the nutritional substance's label, its predicted expiration date value and probabilistic confidence level value.

The hardware layer, 200, further comprises a processor unit, 201, including a CPU, 201A for processing digital signals received from the bio-electronics device; a GPU, 201B responsible for processing the machine learning models for the monitoring and evaluation of nutritional substance label leveraging the Graphical Processing Unit for High Performance Computing and low-latency; the memory unit 202, for storing the digital signals; the Input/output module 203 for capturing multimodal inputs such as audio, touch from user-initiated actions on the bio-analytics platform's user interface; the storage unit 204, for storing the digital signals redundantly and a communication module, 310, responsible for receiving the digital signals communicated from the soft nano-enabled material over the network (not illustrated).

The operating system layer, 210, comprises a system call hook module, 211, for capturing low-level operating system calls for security monitoring. The software layer, 220, further comprises an ETL module 221, a data processing module framework that processes the nutritional substance digital signals received from the bio-electronics device, Machine Learning Models, 222, deployed for monitoring, grading and evaluating the nutritional substance's freshness and/or spoilage, an evaluation agent, 223, that determines a given nutritional substance label, for example, as 'fresh', 'frozen', 'organic', 'nutritious' or 'spoiled', predicts the expiration date value, for example, as '3 days 4 hours' and computes the probabilistic confidence level value, for example, '90%' given an evaluation model and based on threshold value decision making comprising one or more threshold values, and finally a data storage unit 224, that stores the digital signals and processed data in the bio-analytics platform.

Various machine learning models for monitoring, grading and evaluating the nutritional substance can be achieved. In one exemplary embodiment, Machine Learning Models, 222, are implemented using HMM, Hidden Markov Model, a temporal learning probabilistic model for sequences with hidden states tolerating noise. HMM leverages a double-layered stochastic process: an unobserved Markov process $Q:=q_{1:D}$, where the current state is only dependent on its previous state and an observed stochastic process $O:=o_{1:D}$, where the current observation is only generated from the current hidden state. An HMM $\lambda:=\{\pi, A, B\}$ can be expressed in joint distribution as:

$$P(Q, O) = P(q_1)P(o_1 | q_1)\sum_{d=2}^{D} P(q_d | q_{d-1})P(o_d | q_d),$$

where $\pi:=[P(q_1)]$ represents the initial state vector. $A:=[P(q_d|q_{d-1})]$ is the state transition matrix, and $B:=[P(o_d|q_d)]$ the emission matrix. For a continuous observation sequence, emission matrix B can be replaced by the Gaussian Mixture Model (GMM) density $B:=[b_j(O)]:=\{C, \mu, \Sigma\}$ as:

$$b_j(O) = \sum_{m=1}^{M} c_{jm}N(O, \mu_{jm}, \Sigma_{jm}),$$

where M denotes the number of Gaussian mixtures. $C:=[c_{jm}]$ is the mixture coefficient matrix. $\mu:=[\mu_{jm}]$ and $\Sigma:=[\Sigma_{jm}]$ store the mean vector and the covariance matrix of each Gaussian mixture respectively. Given a set of observation sequences O, the objective is to learn the model $\lambda$ for nutritional substance monitoring using the Segmental Rapid Centroid Estimation (RCE)-based training method. Given a trained model $\lambda$ and one observation sequence O, the task entails finding the most likely hidden state sequence Q that generates that observation sequence for determining the nutritional substance freshness level grading. Finally, given a trained model $\lambda$ and one observation sequence O, the subsequent task is to find the likelihood $P(O|\lambda)$ that the model produces this observation sequence to evaluate the nutritional substance.

Figure 3:
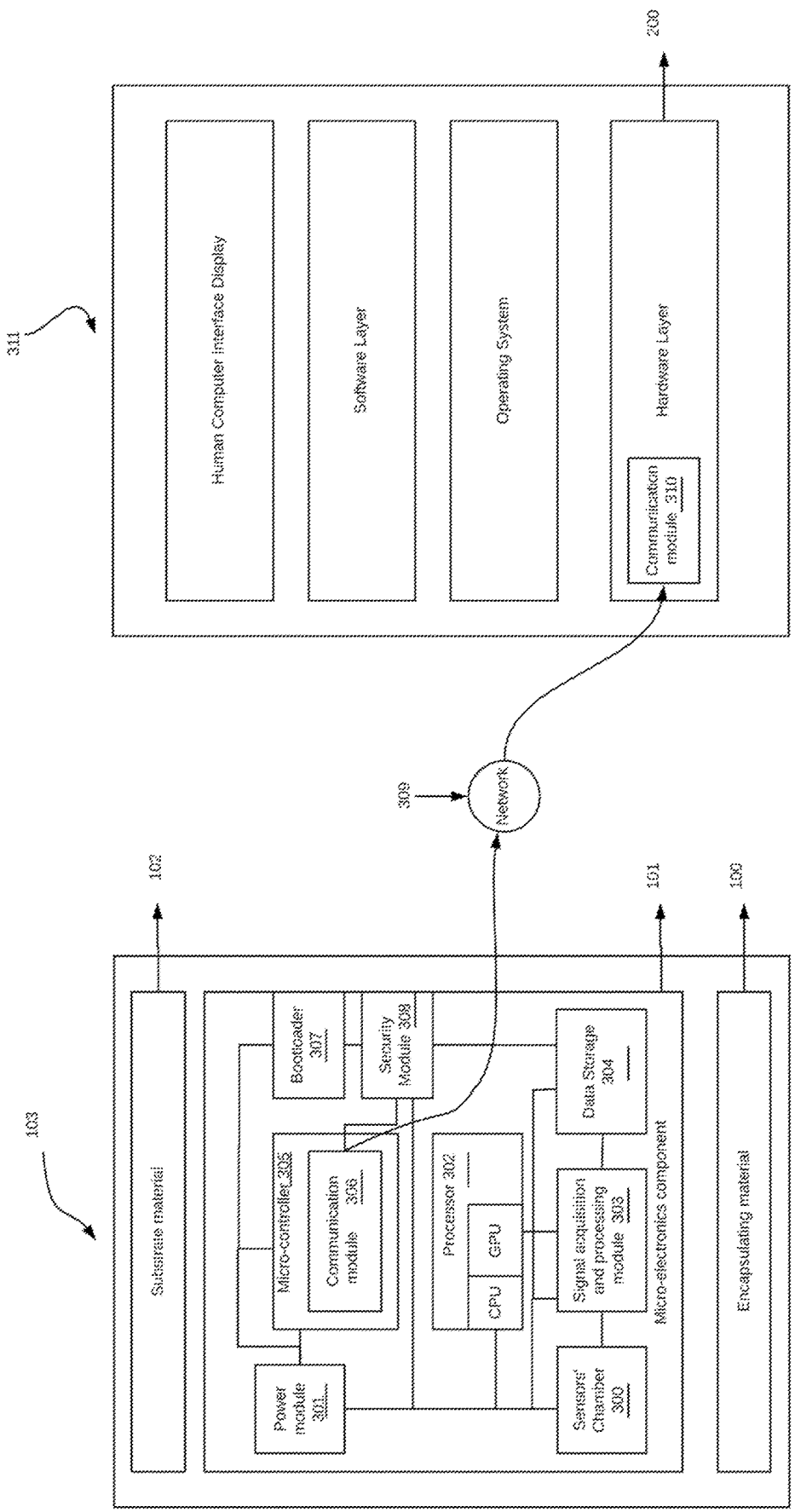
FIG. 3 is a schematic diagram illustrating the signal communication connection between the soft nano-material enabled bioelectronics and the bio-analytics platform.

FIG. 3 is a schematic diagram illustrating the signal communication connection between the soft nano-material enabled bioelectronics 103 and the bio-analytics platform 311. The bio-analytics platform 311 comprises the communication module 310 that receives the digital signals sent from the soft nano-material enabled bioelectronics 103 over the network 309.

Figure 5:
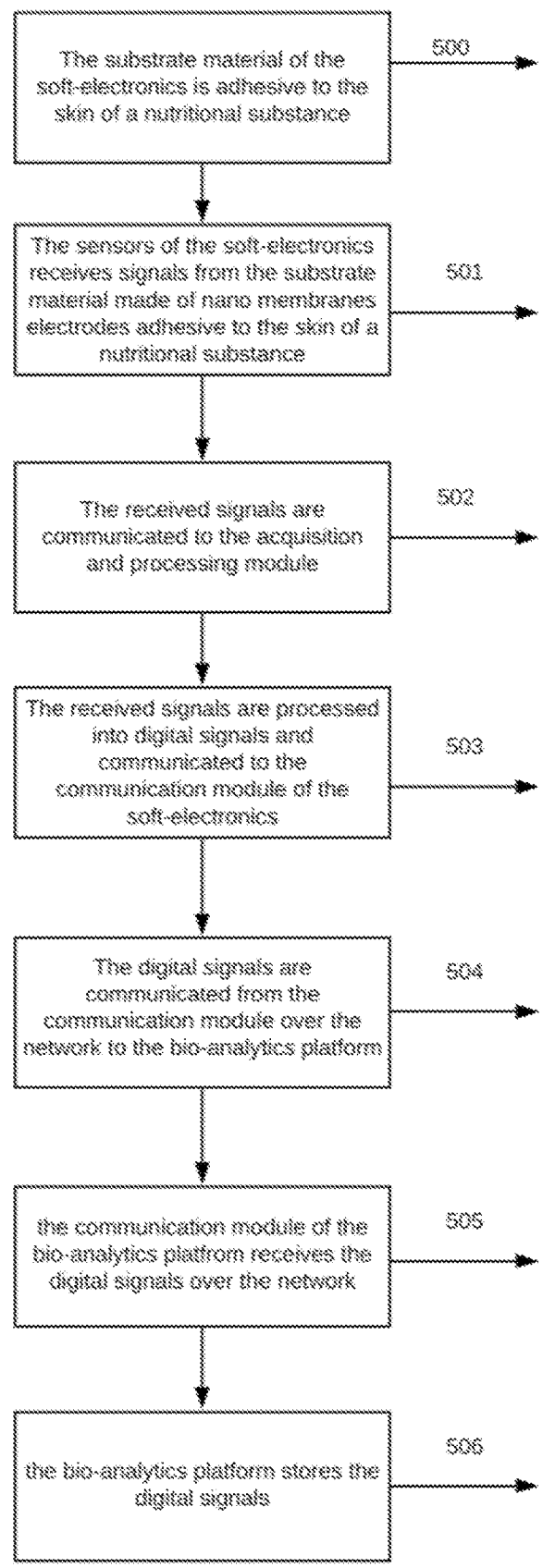
FIG. 5 is a flowchart diagram describing the flow of signals from the soft nano-enabled bio-electronics to the bio-analytics platform.

FIG. 5 illustrates the flowchart diagram describing the flow of signals from the soft nano-enabled bio-electronics to the bio-analytics platform. The first step, 500, represents the substrate material of the soft-electronics adhesive to the skin of a nutritional substance. The second step, 501, depicts the sensors of the soft-electronics receiving the signals from the substrate material made of nano membranes electrodes adhesive to the skin of a nutritional substance. The third step, 502, depicts the received signals being sent to the acquisition and processing module. The fourth step, 503, depicts the digital signals being processed and communicated to the communication module of the soft-electronics. The fifth step, 504, depicts the digital signals being communicated from the communication module over the network to the bio-analytics platform. The sixth step, 505, depicts the communication module of the bio-analytics platform receiving the digital signals over the network. The seventh step, 506, depicts the bio-analytics platform storing the digital signals.

The nutritional substance quality monitoring, grading and evaluation, expiration date prediction and probabilistic confidence level computation of the proposed innovation entails three steps: (1) the learning or training phase of a machine learning model using Segmental RCE algorithm based on fresh nutritional substance sample metadata inputs such as one of the storage temperature in one of the types ('° C.', '° F.') format, storage clock time in hour and/or minutes formats under the given nutritional substance storage temperature, sample name in one of the types (beef, 'turkey', 'lamb', 'fish', 'pork', 'shrimp', 'bread', 'eggs', 'milk', 'flour') format among other nutritional substance name formats, sample type in one of the types ('fruits', 'vegetables', 'dairy', 'bakery', 'meat', 'seafood', 'poultry') format among other nutritional substance type formats, sample 2-dimensional image vector, sample weight in grams format, sample volume in milliliters format, sample state in one of the types ('solid', 'liquid', 'semi-liquid') among other nutritional substance state formats, sample resonant frequency and impedance frequency in one of the types ('KHz', 'MHz', 'GHz', 'THz'), sample phase angle in degrees format, sample peak voltage range in Volt format, sample position in longitude and latitude formats, sample molar concentration of each target gas in parts per million (ppm) or parts per billion (ppb) unit format, sample rate constant of each target gas and an output trained model $\lambda$. (2) the freshness level grading phase to deliver a freshness level grading models $\lambda_{grading}$ based on the Viterbi decoding algorithm applied to the trained model A over a continuous sampled period of time $t_1, t_2, \ldots, T$. The grading model $\lambda_{grading}$ is the highest log-likelihood grading model from a suite of freshness level grading models. (3) the evaluation phase that entails evaluating an incoming sample nutritional substance based on the output trained model A and freshness grading models $\lambda_1, \lambda_2, \ldots, \lambda_T$ for each freshness level, taking the highest log-likelihood model of all trained and freshness grading models with an output that (a) labels the incoming sample, for example, as 'fresh', 'frozen', 'organic', 'spoiled' or 'nutritious', (b) predicts the incoming sample expiration date in days and/or hours format and (c) computes the probability confidence level value, in percentage format, of the incoming sample label value and predicted expiration date.

Determining the freshness level grading models over a continuous sampled period of time entails monitoring fresh nutritional samples from purchase time (t=0) to several days (t>0) under different storage temperature conditions until the nutritional substance degradation process starts and reaches spoilage or expiration.

Figure 6:
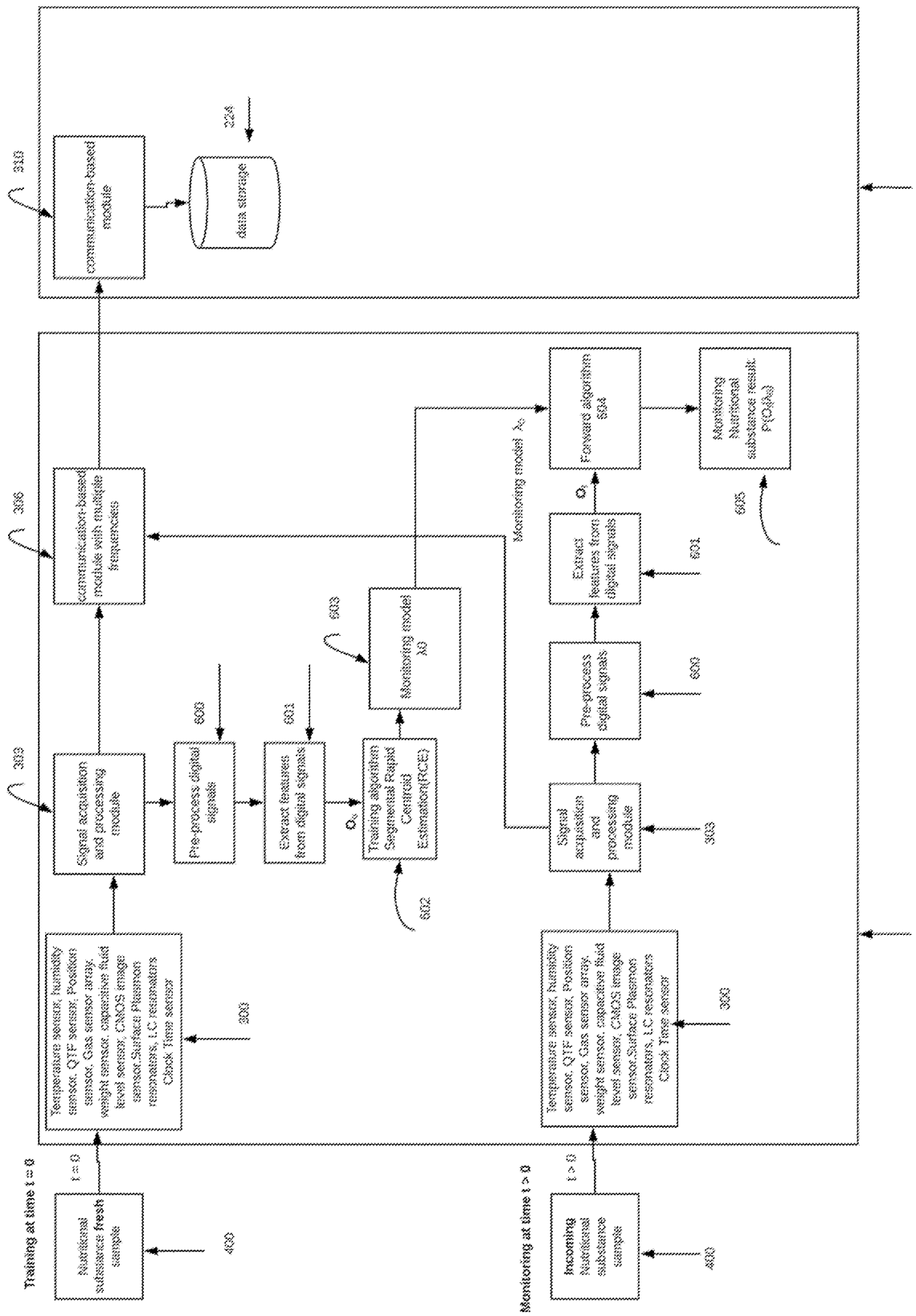
FIG. 6 is a schematic diagram describing the training process of a sample nutritional substance in order to determine the spoilage/expiration date condition under various storage temperature conditions.

FIG. 6 is a schematic diagram describing the training process of a sample nutritional substance. Real-time dynamic and continuous monitoring is necessary to determine a monitoring model over a long period of time and under various storage temperature conditions, that is, for instance, normal temperature 25° C. and refrigerator temperature 4° C. to determine the life span and storage spoilage conditions of the incoming nutritional substance sample.

At the top left side of FIG. 6, a fresh nutritional substance sample, 400, is adhesive to the substrate material of the soft nano-material enabled bio-electronics 103 at training time t=0, that is, at the nutritional substance sample near purchase time. The nano-membrane electrodes of the substrate material enable high electrical properties conductivity to the sensors' array chamber, 300, located on the micro-electronics component of the soft-electronics. The sensors receive signals from the nutritional substance sample such as one of the resonant frequency, the impedance frequency; the impedance phase angles; the voltage range among other dielectric signals. The shifts in the impedance and resonant frequency are used to transduce and monitor the variation of dielectric properties associated with density/firmness and material composition including parameters such as moisture, gas emission, salt content that correlate to the nutritional substance's quality.

In addition, the nutritional substance's temperature, humidity and 2-dimensional image vector are captured from the temperature, humidity and CMOS image sensors respectively. VOC biomarkers detect the odour and transduce the chemical vapors into impulse response signals. The received visual and dielectric signals from the sensors are communicated to the signal acquisition and processing module 303 and amplified to improve the signal-to-noise ratio with low-noise amplifiers. The visual, volatile organic compound and electrical digital signals are communicated to the communication-based module 306. The digital signals are further communicated over the network (not illustrated) to the communication-based module, 310, of the bio-analytics platform 311 and the digital signals are saved in the data storage 224 of the bio-analytics platform for local processing.

VOC impulse responses signals from gas sensors and biomarkers are initially pre-processed to ensure a reliable and stable feature extraction for transient state features. The pre-processing method 600 first encompasses applying the fractional conductance to reduce the effect of the sensor drift; then applying a non-parametric Kernel-Based Modeling (KBM) to smooth the response curve to address the noise sensitivity of transient state features. The relationship between the VOC input (u) which can be treated as a step simulation, and the gas sensor response (y) can be described by a Single Input Single Output (SISO) dynamic system. Given t with sampling time T selected as the time index, the discrete time output y may be calculated by the Impulse Response (IR) with the following question:

$$y(t) = \sum_{k=1}^{\infty} g_k^0 q^{-k} u(t) + \epsilon(t), k = 1, 2, 3 \ldots, \infty$$

$$t = 1, 2, 3, \ldots, N$$

where $g_k^0$ represents the coefficient of the Impulse Response. q represents the shift operator, i.e. $qu(t)=u(t+1)$, $\epsilon(t)$ is the Gaussian white noise.

After pre-processing, nine derivative-based impulse response features 601 are extracted from each of the VOC gas sensors: (f1: feature 1) the response of the peak value, (f2: feature 2) the response of the maximum 1st-order derivative, (f3: feature 3) the response of the maximum 2nd-order derivative, (f4: feature 4) the response of the minimum 2nd-order derivative, (f5: feature 5) the time interval between gas-in and the response of the peak value, (f6: feature 6) the time interval between gas-in and the response of the maximum 1st-order derivative, (f7: feature 7) the time interval between gas-in and the response of the maximum 2nd-order derivative, (f8: feature 8) the time interval between gas-in and the response of the minimum 2nd-order derivative and (f9: feature 9) the integral from the time of bio-electronics adhesion to the nutritional substance to the time of the response of the peak value f1. Therefore, the dimension of the feature vector representing the gas sensor array's response is equal to the product of the number of gas sensors and the nine extracted features.

Various steps to train a machine learning algorithm can be achieved using an Artificial Neural Network (ANN), a Convolutional Neural Network (CNN) or other deep learning machine learning models. In one exemplary embodiment, a Segmental Rapid Centroid Estimation (RCE) training algorithm is used as explained hereinafter. The monitoring model $\lambda_0$ 603 is trained by Segmental RCE algorithm 602 only using the feature vectors of fresh nutritional substance samples $O_o=[o_o^{(1)}, o_o^{(2)}, \ldots, o_o^{(K)}]^T$. Subscript o is used to denote a fresh nutritional substance sample at training time t=0. $O_o^{(K)} \in \Re^{1 \times dim}$ represents the $K^{th}$ fresh nutritional substance sample. The training algorithm, Segmental Rapid Centroid Estimation (RCE), 602, is used to learn the monitoring model $\lambda_0$ 603 using only fresh nutritional sample. The Segmental RCE training algorithm separates the observation sequences into several segments, then estimates Gaussian mixture parameters within each segment. The algorithm converges when the distance between two re-estimated models reaches a threshold. The Segmental RCE is implemented as follows:

---

Input: Observations $O \in \Re^{K \times dim}$, state number N $\in Z^+$ and mixture number $M \in Z^+$
1: Initialize $\lambda$ randomly or according to requirements.
2: iter ← 0.
3: repeat
4: Partition O into N segments as $\{O_1, O_2, \ldots, O_N\}$ according to the optimal path of $\lambda$ calculated via the Viterbi algorithm.
5: for j = 1, 2, ..., N do
6: if $|O_j| < M$, where $O_j = \{o_{j,1}, \ldots, o_{j,T_j}\}$, then 7: $$\forall m, \hat{c}_{jm} \leftarrow \frac{1}{M},$$

8: $$\forall m, \hat{\mu}_{jm} \leftarrow \frac{\Sigma_{o_{j,t} \in o_j} o_{j,t}}{|O_j|},$$

9: $\forall m, \hat{\Sigma}_{jm} \leftarrow$ Identity matrix.
10. else
11: Cluster $O_j$ into M clusters via RCE algorithm, 12: $$\forall m, \hat{c}_{jm} \leftarrow \frac{\text{The number of } o_{j,t} \text{ grouped in cluster } m}{|O_j|},$$

13: $\forall m, \hat{\mu}_{jm} \leftarrow$ the mth centroid of $O_j$,
14: $\forall m, \hat{\Sigma}_{jm} \leftarrow$ cov(All $o_{j,t}$ grouped in cluster m).
15: end if
16: end for
17: $\hat{\lambda} \leftarrow \{\pi, A, \hat{C}, \hat{\mu}, \hat{\Sigma}\}$.
18: $\lambda \leftarrow$ re-estimate $\lambda$ via the Baum - Welch Algorithm.
19: iter ← iter + 1
20: until {Convergence} or {iter reaches the maximum iteration}
21: return Trained model $\lambda = \{\pi, A, C, \mu, \Sigma\}$

---

The referenced RCE algorithm pseudocode is implemented as follows:

Input: Observations O $\in \Re^{K \times dim}$, cluster number M $\in Z^+$.
Output: Locally optimum centroids $\mu_{Best} \in R^{M \times dim}$.
1: Initialize swarm: M particles, where $\mu \leftarrow$ rand($\Omega$), c $\leftarrow$ 0, s $\leftarrow$ 0,
   $\mu_{Best}^0 \leftarrow \mu, \Delta\mu^0 \leftarrow 0$. ▷ $\Omega$: searching space
2: iter $\leftarrow$ 1; stag $\leftarrow$ 0.      ▷ stag: count for stagnation
3: repeat
4: Calculate pairwise Euclidean distance between each $O_k$ and each $\mu_m$.
5: $\forall m, c_m \leftarrow$ The closest position, $\mu_m$, of the particle m in relation to the observation $O_k$.
6: $\forall k, s_k \leftarrow$ The position a particle that has been closest to the observation $O_k$.
7: $\mu_{Best}^{iter} \leftarrow$ arg min$_{\{\mu_{Best}\mu^{iter-1}\}}$ $\{f(\mu_{Best}^{iter-1}), f(\mu)\}$. ▷ f: cost function 8: $stag = \begin{cases} stag+1, & f(\mu_{Best}^{iter}) - f(\mu_{Best}^{iter-1}) > -\epsilon \\ 0, & \text{otherwise} \end{cases}$ 9: $\mu_{win} \leftarrow$ Position of a particle which constituted cluster contains the most observations.
10: Assign each observation to its corresponding cluster $O_m$
11: for m = 1, 2, . . . , M do
12:   if $|O_m| > 0$ then
13:     $C_m \leftarrow c_m - \mu_m$.  ▷ Cognitive term 14: $S_m \leftarrow \dfrac{\sum_{\forall O_k \varepsilon O_m}(s_k - \mu_m)}{|O_m|}$.

▷ Social term

15: $R_m \leftarrow \dfrac{\sum_{\forall O_k \varepsilon O_m}(O_k - \mu_m)}{|O_m|}$.

▷ Self - organising term
16: $\Delta\mu_m^{iter} \leftarrow \omega \cdot \Delta\mu_m^{iter-1} + \phi_1 \circ C_m + \phi_2 \circ S_m + \phi_3 \circ R_m$.
17: $\mu_m \leftarrow \mu_m + \Delta\mu_m^{iter}$.
18:  else
19:    $\mu_m \leftarrow \mu_m + \phi_4 \circ (\mu_{win} - \mu_m)$.
▷ $\circ$: Hadamard product; $\phi_{1...4}$: uniform random vector
20:  end if
21: end for
22: $\omega \leftarrow 0.95 \times \omega$. ▷ $\omega$: inertia weight
23: iter $\leftarrow$ iter + 1
24: until {iter reaches the maximum iteration} or {stag reaches threshold}
25: return Locally optimum centroids $\mu_{Best}$.

The Segmental RCE algorithm is randomly initialized and run 100 times for three test groups: (1) group 1 comprising fresh nutritional substance samples measured the same day the samples were purchased and kept under storage temperature of 4° C.; (2) group 2 comprising fresh nutritional substance samples measured every 8 hour and kept under room storage temperature 25° C. and (3) group 3 comprising fresh nutritional substance samples measured every 8 hour and kept under refrigerator storage temperature of 4° C. The nutritional substance sample measurements are repeated three times for consistency check.

The training process at time t=0 (top left FIG. 6) targets a fresh sample input under group 1 while the process at t>0 (bottom left FIG. 6) targets an incoming sample input from groups 2 and 3, under room temperature and refrigerator temperature respectively. Note that group 1 contributes to monitoring the sample freshness level at purchase time under a cold chain environment while groups 2 and 3 real-time monitoring assess the sample degradation process over sampled time periods and under different storage temperature conditions.

On the bottom left of the figure, an incoming nutritional sample $O_t$ (t>0), 400, is evaluated by the monitoring model $\lambda_0$, 603. Various steps to evaluate the monitoring model $\lambda_0$ can be achieved using k-Nearest Neighbors (k-NN), Principal Component Analysis (PCA) or the like. In one exemplary embodiment, a Forward algorithm, 604, is used as explained hereinafter.

The Forward algorithm is used to calculate a 'belief state': the probability of a state at a certain time, given the history of evidence. The Forward algorithm computes the joint probability $p(x_t, y_{1:t})$ where $x_t$ represents the hidden state at time t and $y_{1:t}$ is the same as $(y(1), y(2), \ldots, y(t))$ representing the observations 1 to t. The forward algorithm is implemented as follows:

1: Input: Initialize t = 0, Transition probabilities T $p(x_t|x_{t-1})$,
   Emission probabilities E $p(y_t|x_t)$, Observed sequence O y(1:t).
2: Output: The probability of a state at a certain time,
   given the history of evidence $\alpha_t = p(y(1:t))$.
3: function FORWARD(t, T, E, O): $\alpha_T$
4: for t = t + 1

5: $\alpha_t(x_t) = p(y_t | x_t) \sum_{x_{t-1}} p(x_t | x_{t-1}) \alpha_{t-1}(x_{t-1})$.

6: until t = T
7: return p(y(1:t)) = $\alpha_T$
8: end function

The monitoring result, 605, output of the forward algorithm, 604, is the log-likelihood, which denotes the probability of the observation generated by the given monitoring model $\lambda_0$. The monitoring result $P(O_t|\lambda_0)$ is expected to maintain a similar value if the incoming nutritional sample is still fresh but will drop to a very low value when the sample has spoiled. The continuous monitoring is achieved by tracking the change of the log-likelihood over time, computing the lowest average log-likelihood recorded value over a storage time period greater than, for example, 280 hours to determine the predicted expiration date of that incoming nutritional substance.

Figure 7:
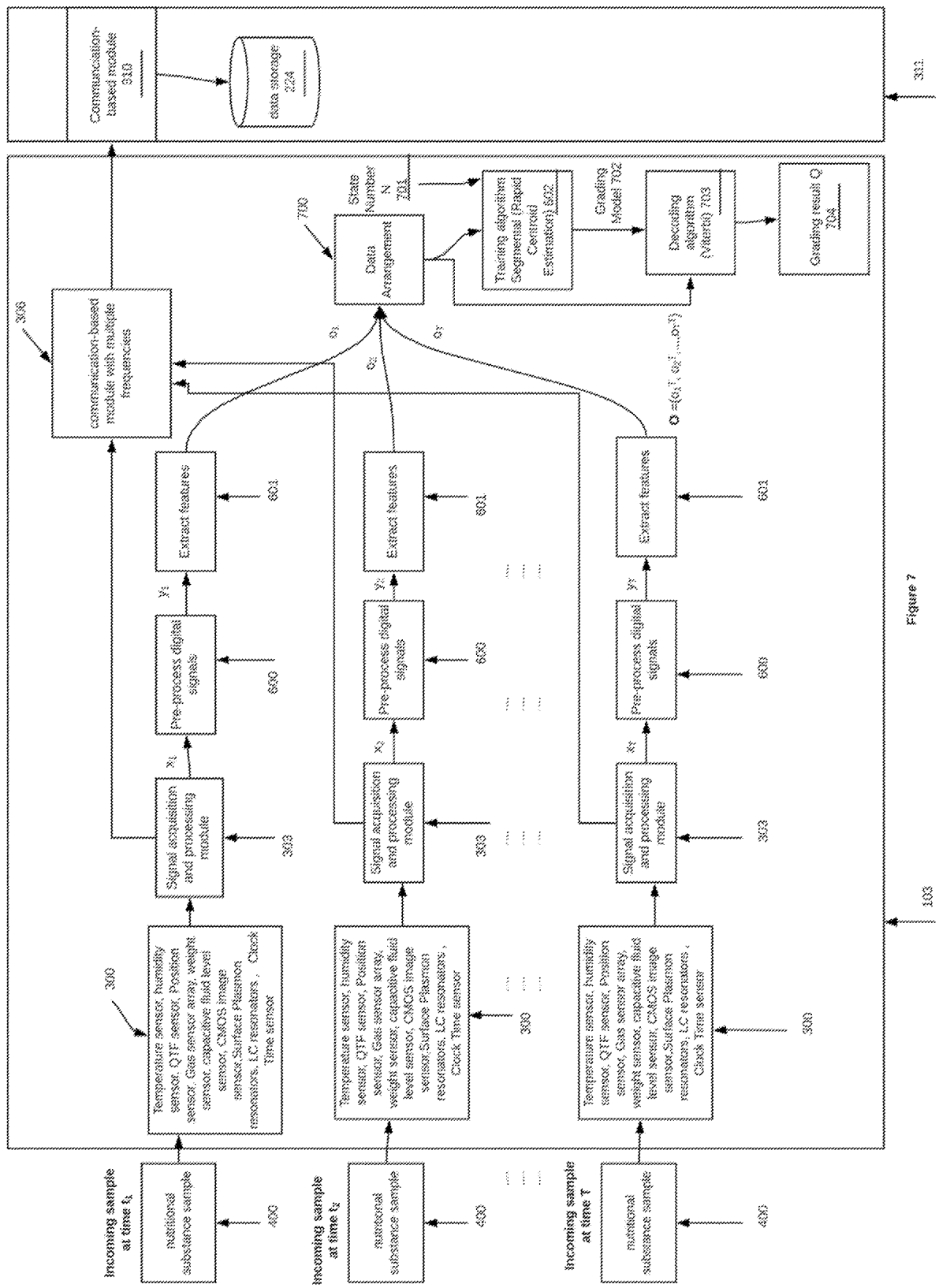
FIG. 7 is a schematic diagram describing the nutritional substance freshness level grading process in order to determine the nutritional substance freshness.

FIG. 7 is a schematic diagram describing the nutritional substance freshness level grading process in order to determine the nutritional substance freshness. To build the freshness level grading model, the entire life-span observation data 700 is arranged in chronological order as O=[$o_1^T$, $o_2^T, \ldots, o_T^T$], where $o_t \in \Re^{1 \times dim}$ is the feature vector of the sample obtained at time t. The initial state vector of the HMM is fixed as $\pi=[1, 0, \ldots, 0]^T \in \Re^N$ during the training procedure 602. The initial guess of state transition matrix A, is as:

$$A = \begin{bmatrix} 0.5 & 0.5 & 0 & \ldots & 0 \\ 0 & 0.5 & 0.5 & \ldots & 0 \\ 0 & 0 & 0.5 & \ldots & 0 \\ \vdots & \vdots & \vdots & \vdots & \vdots \\ 0 & 0 & 0 & \ldots & 1 \end{bmatrix} \in \Re^{N \times N}$$

The training procedure 602 uses the entire life-span samples $t_1, t_2, \ldots$ T from groups 2 and 3 to learn the freshness level grading model 702. Various steps to find a hidden state sequence that is most likely to generate O can be achieved such as Expectation Maximization (EM), Maximum Likelihood (ML) or the like. In one exemplary embodiment, the Viterbi decoding algorithm, 703, is used as explained hereinafter.

After the training procedure 602, the Viterbi decoding algorithm 703 is applied to the freshness level grading model 702 to find a hidden state sequence that is most likely to generate O. The Viterbi algorithm is a suitable dynamic programming algorithm for finding the most likely sequence of hidden states that result in a sequence of observed events with nutritional substance sample dependence on time. Given that nutritional substance spoilage is an irreversible process, where the freshness level degrades progressively with storage time and cannot change back, therefore, the freshness level is modeled as a hidden state since it usually hides beneath the observable feature vectors extracted from the VOC sensors' responses. Regular HMMs can uncover the exact freshness level from the observations. In one exemplary embodiment, the Viterbi algorithm described below uncovers the exact freshness level from the observations using the no jump left-right HMMs.

The Viterbi algorithm pseudocode is implemented as follows:

---

1: Input: Observation space $O = \{o_1, o_2, o_3, \ldots, o_N\}$,
State space $S = \{s_1, s_2, \ldots, s_k\}$,
An array of initial probabilities $\Pi =$
$(\pi_1, \pi_2, \ldots, \pi_k)$ such that $\pi_i$ stores the probability that $x_1 = s_i$.
A sequence of observations $Y = (y_1, y_2, \ldots, y_T)$ such that $y_t = $
i if the observation at time t is $o_i$,
Transition Matrix A of size K × K such that $A_{ij}$ stores the
transition probability of transitioning from state $s_i$ to state $s_j$,
An emission matrix B of size K X N such that $B_{ij}$ stores the probability
of observing $o_j$ from state $s_i$.
2: Output: The most likely hidden state sequence $X =$
$(x_1, x_2, \ldots, x_T)$. The highest probability $\pi$ of observing the most likely hidden state sequence X.
3: function VITERBI (O, S, Π, Y, A, B): (X, π)
4: for each state i = 1, 2, ..., K do
5: $T_1[i, 1] \leftarrow \pi_i \cdot B_{iy_1}$
6: $T_2[i, 1] \leftarrow 0$
7: end for
8: for each observation j = 2, 3, ..., T do
9: for each state i = 1, 2, ..., K do 10: $T_1[i, j] \leftarrow \max_k \left(T_1[k, j-1] \cdot A_{ki} \cdot B_{iy_j}\right)$ 11: $T_2[i, j] \leftarrow \text{argmax}_k \left(T_1[k, j-1] \cdot A_{ki} \cdot B_{iy_j}\right)$ 12: end for
13: end for 14: $Z_T \leftarrow \text{argmax}_k (T_1[k, T])$ 15: $x_T \leftarrow s_{z_T}$
16: for j = T, T - 1, ..., 2 do
17: $z_{j-1} \leftarrow T_2[z_j, j]$
18: $x_{j-1} \leftarrow s_{z_{j-1}}$
19: end for
20: return (X, π)
21: end function

---

The optimal sequence Q, is the grading result 704, output of the Viterbi algorithm. The hidden states number, N, 701, is representative of the number of freshness level, which is determined by the one that maximizes the Bayesian Information Criterion (BIC). The BIC formula follows the Pelleg and Moore's work as $$BIC(N) = \log l(O \mid \lambda; N) - \frac{K_N}{2} \log(|O|)$$

where $l(O\|;N)$ denotes the likelihood of the observation set, O, given the model, $\lambda$, parameterized by N, and $|O|$ denotes the number of samples. $K_N$ represents the number of free parameters and the optimal N is the one that obtains the highest value of the BIC.

After obtaining a grading freshness result 704, the final step entails evaluating a given incoming nutritional substance sample freshness level based on an evaluation model trained with nutritional sample data from groups 2 and 3.

Figure 8:
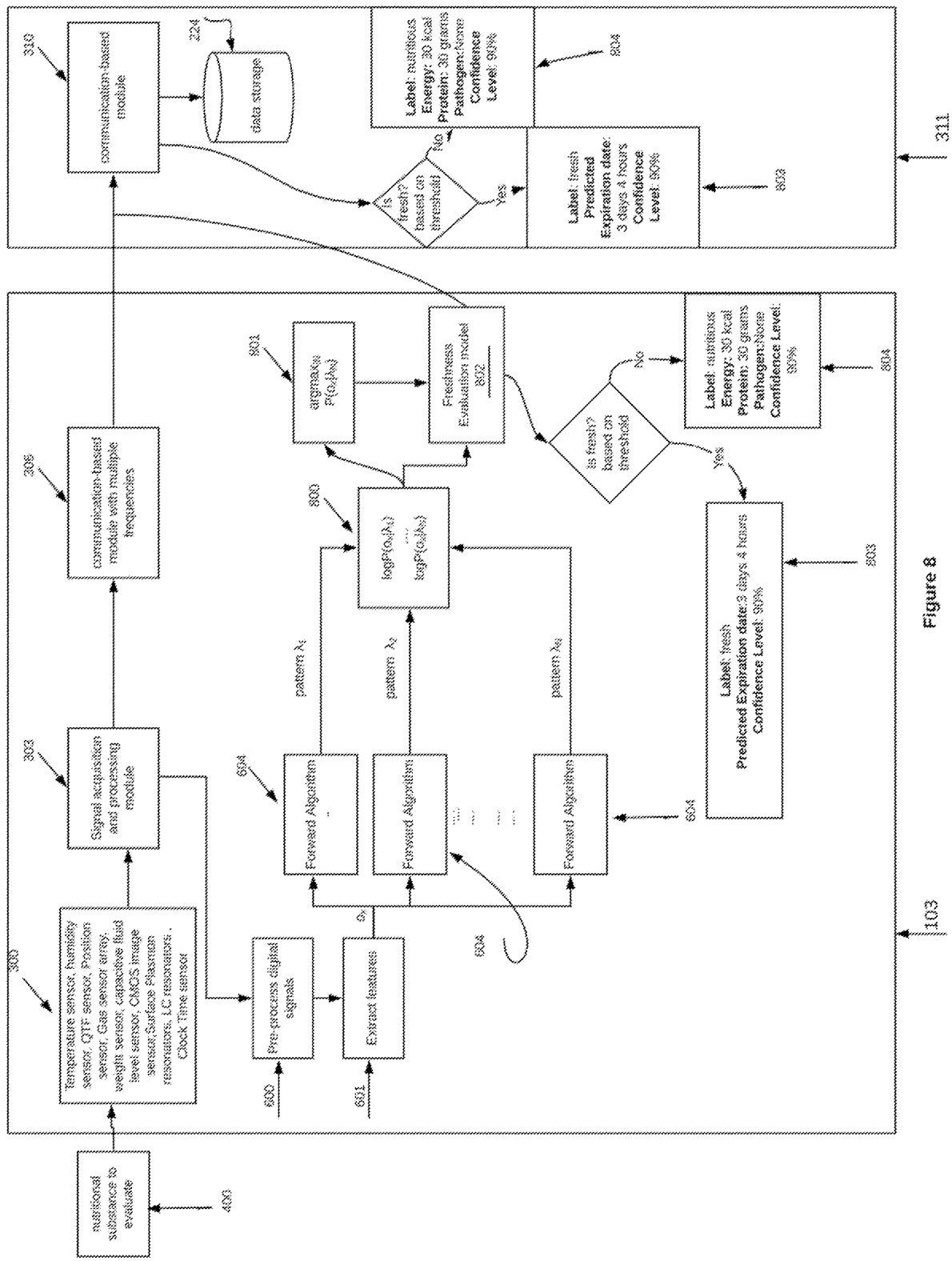
FIG. 8 is a schematic diagram describing the nutritional substance evaluation process in order to evaluate the freshness level of a given nutritional substance.

FIG. 8 illustrates a schematic diagram describing the nutritional substance evaluation process that determines the freshness level of a given nutritional substance.

The pattern of each freshness level $\lambda_1, \lambda_2, \ldots, \lambda_N$ is trained using the data from its corresponding cluster to obtain $P(o_x|\lambda_1), P(o_x|\lambda_2), \ldots, P(o_x|\lambda_N)$ denoting the probability of the observation generated by each freshness level pattern $\lambda$ (not illustrated). During the evaluation process, the log-likelihood log $P(o_x|\lambda_1)$, log $P(o_x|\lambda_2)$, ..., log $P(o_x|\lambda_N)$, 800, of the nutritional substance sample is evaluated by all trained models. Sample data from groups 2 and 3 are used to train the freshness evaluation model 802, which is then used to test whether the nutritional substance sample freshness levels in group 1 are correctly identified. The training operation is performed using the three-fold cross validation, that is, repeated three times to ensure each group was used for training only once.

The freshness evaluation model 802 is determined by the model that achieves the highest log-likelihood, $$\arg\max_{i \in N} \log P(o_x|\lambda_N),$$

801, via the Forward algorithm 604.

The Forward algorithm is run 100 times for each freshness level sample with the sample size of the last freshness level larger than the previous freshness levels.

The freshness evaluation model result 802 is communicated over the network (not illustrated) to the communication-based module 310 of the bio-analytics platform 311. The freshness evaluation model result 802 is communicated to the data storage 224 for redundancy. The evaluation output result (the freshness evaluation model result 802) is evaluated using threshold value decision making comprising one or more threshold values to determine the output result describing at least one of the nutritional substance freshness level label, the nutritional substance predicted expiration date and a probabilistic confidence level value based on all trained models and each freshness level of the grading models. Various label values to determine the nutritional substance value can be achieved such as 'frozen', 'fresh', 'spoiled', 'organic', 'nutritious', 'proteins:50g', 'energy: 30kcal', 'pathogen: None' or the like. In one exemplary embodiment, the label value is, for example, one of 'fresh' 803 with the nutritional substance predicted expiration date, for example, set to '3 days 4 hours' depicting the lowest average log-likelihood over a 280 hour storage time period, and the confidence level probability value, for example, set to '90%' and depicting the highest probability associated with the displayed label and predicted expiration date values. In another example, the label value is set to 'nutritious', 'energy:30kcal', 'proteins:30 grams', 'pathogen:None', 804, with the confidence level probability value set to '90%'.

In order to obtain the nutrient qualitative and quantitative data along with the pathogen category found in the nutritional substance, the machine learning model 603 is trained with two additional datasets: a first dataset comprising (a) the list of nutritional substance name, (b) each nutritional substance comprising a list of nutrients found in the nutritional substance and (c) the nutrient value associated with each nutrient. The list of nutrients includes protein, carbohydrate, sugars, total fat, cholesterol, thiamin, vitamin A, riboflavin and the like while the nutrient value comprises quantitative data depicted in grams, milligrams, kilocalorie or other nutrient value formats. The second dataset comprising (d) the list of common food pathogens, for example, *Salmonella, E-coli, Shigella*, (e) the electrical properties (quantitative voltage range) at which each pathogen is detected in the nutritional substance and (f) a binary flag indicating whether a given pathogen is present in the nutritional substance. The two datasets are fed as inputs to the machine learning model 603 for training. When a nutritional substance sample 400 is evaluated for nutritional value, the CMOS image based sensor captures, identifies and matches the nutritional substance name from the list of nutritional substances found in one dataset, then the list of nutrients and nutrient value of the identified nutritional substance is returned as outputs from the trained machine learning model. Moreover, the electrical properties captured from the nano-electrodes adhesive to or in the nutritional substance are compared to the electrical voltage range at which each pathogen name is detected from the second dataset. The binary flag indicating whether a given pathogen is present in the nutritional substance is returned as output based on that comparison.

In order to obtain the organic percentage data found in the nutritional substance, the machine learning model 603 is trained with a third dataset comprising (g) the list of nutritional substance name, (h) each nutritional substance comprising a list of ingredients (solid and liquid) found in the nutritional substance and (i) the list of organic ingredients found in the nutritional substance. (j) the weight of each ingredient found in the nutritional substance excluding salt and water. (k) the volume of each liquid ingredient found in the nutritional substance excluding water. The list of ingredients includes tomato, orange juice, soy and the like with the ingredient weight data depicted in grams, milligrams or other weight data formats and the ingredient volume depicted in milliliters, pounds or other volume data formats. The third dataset is fed as input to the machine learning model 603 for training. When a nutritional substance sample 400 is evaluated for nutritional value, the CMOS image based sensor captures, identifies and matches the nutritional substance name from the list of nutritional substances found in the third dataset, then the organic content of the identified nutritional substance is computed as the ratio of the total volume or total net weight of all organic ingredients and the total volume or total weight of all combined ingredients excluding water and salt. The trained machine learning model output returns the nutritional substance 'organic' label if the computed ratio is 95% or greater.

It will be understood that no limitation of the scope of the claimed technology is thereby intended with such alterations and further modifications of these embodiments and further applications of the principles of the claimed technology as illustrated therein being contemplated as would typically occur to one skilled in the art in which the claimed technology relates. For instance, the soft nano-material enabled bio-electronics described here has multi-industry potential and may be used not only for monitoring, predicting and evaluating food quality and expiration date labeling but also food safety, for example, detecting pathogenic micro-organisms such as *E-coli, Salmonella, Campylobacter* or the like in food and beverage products using dielectric properties from the food or beverage products. It can also be used for monitoring and reporting animals' vital signals for medical attention; for monitoring and reporting subjects' position data points within a security perimeter; for tracking livestock pathogenic diseases such as swine flu, avian influenza or the like; or for use as an identification wearable biometric device for port of entry access.

What is claimed is:

1. A computer-implemented nano membrane method for monitoring food freshness to improve access to fresh, healthy food, by determining nutritional value comprising:
   obtaining signals representing properties of a nutritional substance from one or more nano membrane electrodes of a soft nano-material enabled bio-electronics coupled to the nutritional substance;
   receiving the obtained signals;
   pre-processing the received signals by time-frequency signal processing into digital signals; wherein pre-processing the received signals comprises: sampling the received signals;
   amplifying the received signals; applying fractional conductance to reduce an effect of sensor drift; applying a model to smooth a digital signal output response curve; determining an identity of the nutritional substance from the received signals, determining a location of the nutritional substance from the received signals; determining molar concentration and sample rate constant of a volatile organic compound from the received signals;
   extracting temporal and impulse response features from the digital signals;
   using algorithms to convert the extracted features into output values by a trained temporal learning model;
   post-processing the output values by threshold value decision making in order to determine nutritional value; and displaying the nutritional value properties to a user interface.

2. The computer-implemented nano membrane method for monitoring food freshness to improve access to fresh, healthy food, by determining nutritional value according to claim 1, wherein the algorithms include machine learning algorithms.

3. A computer-implemented nano membrane method for monitoring food freshness to improve access to fresh, healthy food, by determining nutritional value comprising:
   obtaining signals representing properties of a nutritional substance from one or more nano membrane electrodes of a soft nano-material enabled bio-electronics coupled to the nutritional substance;
   receiving the obtained signals;
   pre-processing the received signals by time-frequency signal processing into digital signals;
   extracting temporal and impulse response features from the digital signals;
   using algorithms to convert the extracted features into output values by a trained temporal learning model;
   post-processing the output values by threshold value decision making in order to determine the nutritional value; and displaying the nutritional value properties to a user interface;
   wherein converting the extracted features into the output values by the trained temporal learning model comprises using fresh nutritional substance input data to train a machine learning model to obtain a monitoring model, delivering freshness level grading models by using a nutritional substance input data over continuous sampled period of time and different storage temperature conditions to obtain freshness level grading models; determining an evaluation model based on the monitoring model and the freshness level grading models.

4. The computer-implemented nano membrane method for monitoring food freshness to improve access to fresh, healthy food, by determining nutritional value according to claim 3, wherein the algorithms include machine learning algorithms.

5. A computer-implemented nano membrane method for monitoring food freshness to improve access to fresh, healthy food, by determining nutritional value comprising:
- obtaining signals representing properties of a nutritional substance from one or more nano membrane electrodes of a soft nano-material enabled bio-electronics coupled to the nutritional substance;
- receiving the obtained signals;
- pre-processing the received signals by time-frequency signal processing into digital signals;
- extracting temporal and impulse response features from the digital signals;
- using algorithms to convert the extracted features into output values by a trained temporal learning model;
- post-processing the output values by threshold value decision making in order to determine the nutritional value; and displaying the nutritional value properties to a user interface;
- wherein the temporal learning model is trained by steps comprising randomly initializing a model into an initial model, separating incoming fresh nutritional samples data into several segments, estimating a Gaussian mixture parameters within each segment, re-estimating the initial model to an estimated model, determining the trained temporal learning model based on convergence, wherein convergence is determined when a distance between the initial model and the estimated model reaches a threshold.

6. The computer-implemented nano membrane method for monitoring food freshness to improve access to fresh, healthy food, by determining nutritional value according to claim 5, wherein the temporal learning model comprises fresh nutritional samples data measured at a time of purchase.

7. The computer-implemented nano membrane method for monitoring food freshness to improve access to fresh, healthy food, by determining nutritional value according to claim 5, wherein the algorithms include machine learning algorithms.

8. A computer-implemented nano membrane method for monitoring food freshness to improve access to fresh, healthy food, by determining nutritional value comprising:
- obtaining signals representing properties of a nutritional substance from one or more nano membrane electrodes of a soft nano-material enabled bio-electronics coupled to the nutritional substance;
- receiving the obtained signals;
- pre-processing the received signals by time-frequency signal processing into digital signals;
- extracting temporal and impulse response features from the digital signals;
- using algorithms to convert the extracted features into output values by a trained temporal learning model;
- post-processing the output values by threshold value decision making in order to determine the nutritional value; and displaying the nutritional value properties to a user interface;
- wherein freshness level grading models comprise separating nutritional samples into three groups: fresh nutritional samples measured stored under refrigerator temperature; fresh nutritional samples measured every 8 hours under refrigerator storage temperature; and fresh nutritional samples measured every 8 hours at normal room storage temperature.

9. The computer-implemented nano membrane method for monitoring food freshness to improve access to fresh, healthy food, by determining nutritional value according to claim 8, wherein the algorithms include machine learning algorithms.

10. A computer-implemented nano membrane method for monitoring food freshness to improve access to fresh, healthy food, by determining nutritional value comprising:
- obtaining signals representing properties of a nutritional substance from one or more nano membrane electrodes of a soft nano-material enabled bio-electronics coupled to the nutritional substance;
- receiving the obtained signals;
- pre-processing the received signals by time-frequency signal processing into digital signals;
- extracting temporal and impulse response features from the digital signals;
- using algorithms to convert the extracted features into output values by a trained temporal learning model;
- post-processing the output values by threshold value decision making in order to determine the nutritional value; and displaying the nutritional value properties to a user interface; wherein post-processing the output values comprises determining the nutritional value based on a monitoring model and freshness level grading models for each freshness level, wherein a number of freshness level represents a highest value of all the freshness level grading models.

11. The computer-implemented nano membrane method for monitoring food freshness to improve access to fresh, healthy food, by determining nutritional value according to claim 10, wherein the algorithms include machine learning algorithms.

12. A computer-implemented nano membrane method for monitoring food freshness to improve access to fresh, healthy food, by determining nutritional value comprising:
- obtaining signals representing properties of a nutritional substance from one or more nano membrane electrodes of a soft nano-material enabled bio-electronics coupled to the nutritional substance;
- receiving the obtained signals;
- pre-processing the received signals by time-frequency signal processing into digital signals;
- extracting temporal and impulse response features from the digital signals;
- using algorithms to convert the extracted features into output values by a trained temporal learning model;
- post-processing the output values by threshold value decision making in order to determine the nutritional value; and displaying the nutritional value properties to a user interface; wherein the threshold value decision making is obtained by deriving a nutritional label, a predicted expiration date value and a probabilistic confidence level value computed based on the monitoring model, and the freshness level grading models.

13. The computer-implemented nano membrane method for monitoring food freshness to improve access to fresh, healthy food, by determining nutritional value according to claim 12, wherein the algorithms include machine learning algorithms.

14. A computer-implemented nano membrane method for monitoring food freshness to improve access to fresh, healthy food, by determining nutritional value comprising:
- obtaining signals representing properties of a nutritional substance from one or more nano membrane electrodes of a soft nano-material enabled bio-electronics coupled to the nutritional substance;

receiving the obtained signals;
pre-processing the received signals by time-frequency signal processing into digital signals;
extracting temporal and impulse response features from the digital signals;
using algorithms to convert the extracted features into output values by a trained temporal learning model;
post-processing the output values by threshold value decision making in order to determine the nutritional value; and displaying the nutritional value properties to a user interface; wherein displaying the nutritional value properties comprises displaying the nutritional substance name, the nutritional substance label value, the nutritional substance predicted expiration date, and the nutritional substance location data points based on the signals received from the nutritional substance.

15. The computer-implemented nano membrane method for monitoring food freshness to improve access to fresh, healthy food, by determining nutritional value according to claim 14, wherein the algorithms include machine learning algorithms.

16. A system to monitor food freshness to improve access to fresh, healthy food, by determining nutritional value of a nutritional food substance, the system comprising:
at least one processor receiving signals representative of properties of the nutritional food sub stance;
one or more nano membrane electrodes of a soft nano-material enabled bio-electronics coupled to the nutritional food substance, the one or more nano membrane electrodes providing the signals;
a pre-processor converting the signals into digital signals by time-frequency signal processing; wherein the pre-processor samples the signals; amplifies the signals; applies fractional conductance to reduce an effect of sensor drift; applies a model to smooth a digital signal output response curve; determines an identity of the nutritional food substance from the received signals; determines a position of the nutritional food substance from the received signals; determines molar concentration and sample rate constant of a volatile organic compound from the received signals;
an extractor obtaining temporal and impulse response features from the digital signals;
a convertor using one or more algorithms to convert the extracted temporal and impulse features into output values with a trained temporal learning model;
a post-processor using threshold value decision making wherein nutritional value is determined from the output values;
a display presenting the nutritional value to a user interface.

17. The system to monitor food freshness to improve access to fresh, healthy food, by determining nutritional value of a nutritional food substance of claim 16 wherein the soft nano-material enabled bio-electronics is coupled to the nutritional food substance by adhesion.

18. The system to monitor food freshness to improve access to fresh, healthy food, by determining nutritional value of a nutritional food substance of claim 16 wherein the algorithms include machine learning algorithms.

19. A system to monitor food freshness to improve access to fresh, healthy food, by determining nutritional value of a nutritional food substance, the system comprising:
at least one processor receiving signals representative of properties of the nutritional food substance;
one or more nano membrane electrodes of a soft nano-material enabled bio-electronics coupled to the nutritional food substance, the one or more nano membrane electrodes providing the signals;
a pre-processor converting the signals into digital signals by time-frequency signal processing;
an extractor obtaining temporal and impulse response features from the digital signals;
a convertor using one or more machine learning algorithms to convert the extracted temporal and impulse features into output values with a trained temporal learning model;
a post-processor using threshold value decision making wherein nutritional value is determined from the output values;
a display presenting the nutritional value to a user interface;
wherein the extracted temporal and impulse features are converted into the output values by using fresh nutritional food substance input data to train a machine learning model to obtain a monitoring model; delivering freshness level grading models by using a nutritional food substance input data over continuous sampled period of time and different storage temperature conditions to obtain freshness level grading models; determining an evaluation model based on the monitoring model and the freshness level grading models.

20. The system to monitor food freshness to improve access to fresh, healthy food, by determining nutritional value of a nutritional food substance of claim 19 wherein the soft nano-material enabled bio-electronics is coupled to the nutritional food substance by adhesion.

21. The system to monitor food freshness to improve access to fresh, healthy food, by determining nutritional value of a nutritional food substance of claim 19 wherein the algorithms include machine learning algorithms.

22. A system to monitor food freshness to improve access to fresh, healthy food, by determining nutritional value of a nutritional food substance, the system comprising:
at least one processor receiving signals representative of properties of the nutritional food sub stance;
one or more nano membrane electrodes of a soft nano-material enabled bio-electronics coupled to the nutritional food substance, the one or more nano membrane electrodes providing the signals;
a pre-processor converting the signals into digital signals by time-frequency signal processing;
an extractor obtaining temporal and impulse response features from the digital signals;
a convertor using one or more algorithms to convert the extracted temporal and impulse features into output values with a trained temporal learning model;
a post-processor using threshold value decision making wherein nutritional value is determined from the output values;
a display presenting the nutritional value to a user interface;
wherein the temporal learning model is trained by randomly initializing a model into an initial model, separating incoming fresh nutritional food samples data into several segments, estimating Gaussian mixture parameters within each segment, re-estimating the initial model to an estimated model, determining the trained temporal learning model based on convergence, wherein convergence is determined when distance between the initial model and the estimated model reaches a threshold.

23. The system to monitor food freshness to improve access to fresh, healthy food, by determining nutritional value of a nutritional food substance of claim 22 wherein the soft nano-material enabled bio-electronics is coupled to the nutritional food substance by adhesion.

24. The system to monitor food freshness to improve access to fresh, healthy food, by determining nutritional value of a nutritional food substance of claim 22 wherein the algorithms include machine learning algorithms.

* * * * *